US006511939B1

(12) United States Patent
Burns et al.

(10) Patent No.: US 6,511,939 B1
(45) Date of Patent: Jan. 28, 2003

(54) CORONATINE AS AN ABSCISSION AGENT

(75) Inventors: Jacqueline Kay Burns, Auburndale, FL (US); Carol Bender, Stillwater, OK (US)

(73) Assignees: The Board of Regents for the Oklahoma Agricultural & Mechanical Colleges, Stillwater, OK (US); University of Florida, Gainesville, FL (US)

( * ) Notice: Subject to any disclaimer, the term of this patent is extended or adjusted under 35 U.S.C. 154(b) by 0 days.

(21) Appl. No.: 09/897,831

(22) Filed: Jun. 29, 2001

(51) Int. Cl.$^7$ .......................... A01N 37/30; A01N 63/02
(52) U.S. Cl. ........................ 504/117; 504/171; 504/334
(58) Field of Search ............................... 504/117, 171, 504/334

(56) References Cited

U.S. PATENT DOCUMENTS 5,674,701 A * 10/1997 Ecker et al. .................. 435/32

OTHER PUBLICATIONS

Ferguson, et al., "Stimulation of Ethylene Production in Bean Leaf Discs by the Pseudomonad Phytotoxin Coronatine", *Plant Physiology*, 77:969–973 (1985).

Kenyon, et al., "The Stimulation of Ethylene Synthesis in Nicotiana tabacum Leaves by the Phytotoxin Coronatine", *Plant Physiology*, 100:219–224 (1992).

Palmer, et al., "Effects of Environmental and Nutritional Factors on Production of the Plyketide Phytotoxin Coronatine by Pseudomonas syringae pv Glycinea", *Applied and Environmental Microbiology*, vol. 59, pp. 1619–1626 (1993).

Koda, et al., "Similarities of the Biological Activities of Coronatine and Coronafacic Acid to those of Jasmonic Acid", *Phytochemistry*, vol. 41, No. 1, pp. 93–96 (1996).

Bender, et al., "Pseudomonas syringae Phytotoxins: Mode of Action, Regulation and Biosynthesis by Peptide and Polyketide Synthetases", *Microbiology and Molecular Biology Review*, 63:266–292 (1999).

Hiraga, et al., "Wound–Induced Expression of a Tobacco Peroxidase is not Enhanced by Ethephon and Suppressed by Methyl Jasmonate and Coronatine", *Plant Cell Physiology*, 41(2):165–170 (2000).

Laudert, et al., "Transgenic Nicotiana tabacum and Arabidopsis thaliana Plants Overexpressing Allene Oxide Synthase", *Planta*, 211:163–165 (2000).

Tamogami, et al., "Coronatine Elicits Phytoalexin Production in Rice Leaves (Oryza sativa L.) in the same Manner as Jasmonic Acid", *Phytochemistry*, 54:689–694 (2000).

Hartmond, et al., "Citrus Fruit Abscission Induced by Methyl–Jasmonate", *J. Amer. Soc. Hort. Sci.*, 125(5):547–552 (2000).

Kender, et al., "Methyl Jasmonate and CMN–Pyrazole Applied Alone and in Combination can Cause Mature Orange Abscission", *Scientia Horticulturae*, 88:107–120 (2001).

* cited by examiner

Primary Examiner—S. Mark Clardy
(74) Attorney, Agent, or Firm—Lisa M. W. Hillman; McDonnell Boehnen; Hulbert & Berghoff

(57) ABSTRACT

The invention provides methods for and compositions comprising coronatine and surfactant for inducing abscission of fruit in plants and trees.

25 Claims, 3 Drawing Sheets

CORONATINE AS AN ABSCISSION AGENT

BACKGROUND OF THE INVENTION

Abscission is the ability of plants to slough off organs, such as fruit, by an active separation of cells. Abscission results from the formation of a starch-filled abscission layer of cells in the area of the fruit rind, which separates the stem from the fruit. Abscission occurs as cells in the abscission layer begin to separate, eventually dropping the fruit from the stem.

Commercial harvesting of fruit can require deviation from the natural abscission cycle. When harvesting takes place where the abscission layer has not begun to separate, a great deal of force can be required to remove the fruit. The force can damage the fruit or the plant. Presently available abscission agents, such as ethephon, can cause unwanted defoliation, gummosis, immature fruit drop, and rind damage. Abscission agents are needed that do not cause these undesirable side effects.

SUMMARY OF THE INVENTION

It is an object of the invention to provide methods and compositions for inducing fruit abscission in plants and trees. This and other objects of the invention are provided by one or more of the embodiments described below.

One embodiment of the invention provides a composition for inducing abscission comprising coronatine and one or more surfactants. The surfactant can be, for example, Tween®-20 ((sorbitan mono-9 octadecenoate poly(oxy-1,1-ethanedlyl)) or Kinetic® proprietary blend of poloyalkylene oxide modified polydimethyl siloxane and non-ionic surfactant. The volume by volume of the surfactant can be about 1.0% to about 0.01%. Preferably, the concentration of coronatine is about 10 mg/L to about 1,000 mg/L. More preferably, the concentration of coronatine is about 50 mg/L to about 500 mg/L. Even more preferably, the concentration of coronatine is about 100 mg/L to about 300 mg/L.

Another embodiment of the invention provides a method of inducing fruit abscission comprising administering an effective amount of coronatine to a fruit-bearing plant or tree. The fruit-bearing plant or tree can be, for example, citrus, such as orange, apple, or cherry.

Even another embodiment of the invention provides a method of harvesting fruit from a plant or tree. The method comprises administering an effective amount of coronatine to a fruit-bearing plant or tree and exerting sufficient force on the fruit to separate the fruit from the plant or tree. The harvesting can be accomplished by manual or mechanical methods.

Thus, the invention provides methods and compositions for inducing fruit abscission without excessive defoliation or gummosis, immature fruit drop, or rind damage.

DETAILED DESCRIPTION OF THE INVENTION

Coronatine

Figure 1:
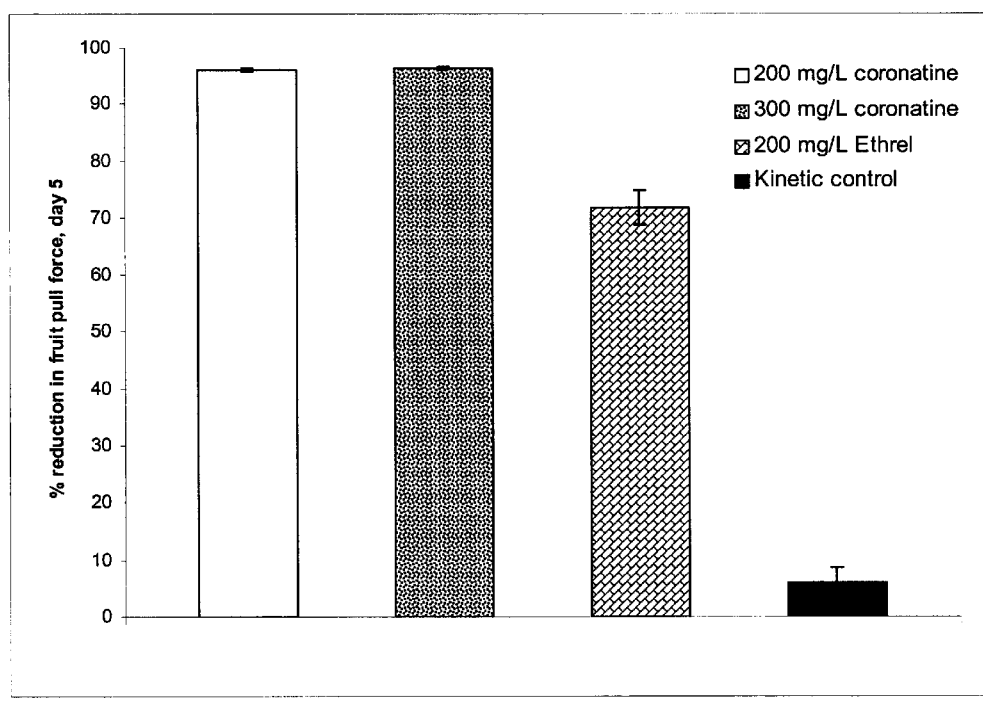
FIG. 1 demonstrates the effect of 200 mg/L and 300 mg/L coronatine, 200 mg/L Ethrel®, and a 0.125% Kinetic® alone treatment on percent reduction of fruit pull-force in Valencia orange. Data are the means of 10 replicate branches, with 10 fruit/branch. Bars above and below the means indicate standard error of the mean.

Coronatine (COR) is a phytotoxin comprised of two distinct components, the polyketide coronafacic acid (CFA) and coronamic acid (CMA), an ethylcyclopropyl amino acid. COR is produced by several pathovars of *Pseudomonas syringae*. See Bender et al., *Microbiol. Mol. Biol. Rev.* 63:266–292 (1999). Genes required for synthesis of COR have been cloned and characterized. See Bender et al.

While COR is a phytotoxin, it does not act as a phytotoxin on trees and plants of the invention, and in particular does not act as a phytotoxin to citrus. It has now been discovered for the first time that COR, COR derivatives and COR analogues are useful as abscission agents. A COR derivative is derived from COR either directly or by modification or substitution and has similar biological activity to COR. A COR analogue is structurally similar to COR and has similar biological activity to COR. Similar biological activity means having 5%, 10%, or 15% greater or lesser biological activity than COR. COR compositions of the invention promote abscission of fruit from fruit-bearing plants and trees without excessive defoliation or gummosis, immature fruit drop, or rind damage. Therefore, compositions of the invention can be applied to fruit-bearing plants and trees as an abscission agent to promote the loosening of fruit without undesirable side effects.

COR can be chemically synthesized in a laboratory. COR can also be obtained from cultures of microorganisms that produce COR, either naturally or recombinantly. For example, COR can be produced in vitro by *P. syringae* strain PG4180.N9 or other high COR-producing strain. A starter culture is prepared by inoculating, for example, a high COR-producing *P. syringae* strain, into 10 mL of broth containing 10 g/L mannitol, 2 g/L L-glutamic acid, 0.5 g/L $KH_2PO_4$, 0.2 g/L NaCl, 0.2 g/L $MgSO_4$ and 0.35 g/L yeast extract, pH 7.0. Before inoculation, 10 μg/mL kanamycin is added. The starting culture is incubated for 48 hours in an incubator-shaker operating at 200 rpm and 28° C.

A fermentation culture is prepared by adding 25 mL of a starting culture to 1 L broth solution containing 450 mL HSC medium A (1 g/L $NH_4Cl$, 0.2 g/L $MgSO_4$, 4.1 g/L $KH_2PO_4$, 0.3 g/L $KNO_3$, and 10 mL of a solution of 2 mM $FeCl_3$, pH 6.8) and 50 mL HSC medium B (20% glucose). Before inoculation of the fermentation culture with the starting culture, 10 μ/mL kanamycin is added. The fermentation culture is incubated for 6 days at 18° C. in an incubator-shaker operating at 200 rpm.

The fermentation culture is centrifuged for 20 minutes at 5,000×g at 4° C. The pellet is discarded. The pH of the supernatant is adjusted to 2.5 with 1 N HCl. The supernatant containing COR is partitioned three times against ethyl acetate (120 mL ethyl acetate: 100 mL supernatant). The aqueous phases are discarded. The organic phases are combined and concentrated to 15 mL under vacuum at 35° C. The concentrate is partitioned three times against a solution of 50 mM sodium carbonate, pH 10.5 (15 mL sodium carbonate solution: 15 mL concentrate). The organic phases are discarded. The aqueous phases are combined and the pH is adjusted to 2.5 with 1 N HCl. The aqueous phase is partitioned three times against ethyl acetate (15 mL aqueous:15 mL ethyl acetate). The aqueous phases are discarded and the organic phases are combined. Excess water from the organic phase is removed by adding 5 g anhydrous sodium sulfate and gently agitating. The organic phase is decanted and evaporated to dryness under vacuum at 35° C. The COR is resuspended in 20 mL methanol. 0.5 mL of the suspension can be removed for quantitation using HPLC as described in Palmer and Bender (Appl. Environ. Microbiol. 59:1619–1626 (1993)). The remainder of the suspended COR is evaporated to dryness and stored at −80° C., if necessary. Typically, 100 mL of starter culture yields 30 mg of COR.

COR can be produced using fermentation techniques well known to those of skill in the art. For example, COR can be made using batch, fed-batch, semi-batch, or continuous fermentation.

COR compositions of the invention are preferably formulated for use in a mixture with one or more plant-compatible surfactants, to provide solid or liquid (including a suspension of a solid in a liquid phase) formulations. A plant-compatible surfactant causes little or no damage to plants or trees. Surfactants of the invention can be nonionic, anionic, cationic, or zwitterionic surfactants. A surfactant can be present in a composition of the invention as formulated or, alternatively, a surfactant can be introduced to the compositions of the invention during application to the plant or tree. Preferably, a surfactant is Kinetic® (Setre Chemical Co., Memphis, Tenn.), Silwet L-77® (polyalkylene oxide modified heptamethyl trisiloxane) (OSi Specialties, Danbury, Conn.), or Tween® 20 (Sigma-Aldrich, St. Louis, Mo.). Preferably, a surfactant used at a final concentration of about 1.0 to 0.01% (volume by volume). More preferably, a surfactant is used at a final concentration of about 0.5 to 0.05%. Even more preferably, a surfactant is used at a final concentration of about 0.125%.

The compositions can be applied in a mixture with a carrier, or optionally, other auxiliary agents from any one of the standard types of preparations commonly used in agriculture, for example, a dry blend, granules, a wettable powder, an emulsion, and an aqueous solution. Suitable carriers for solid formulations include clay, talc, kaolin, bentonite, terra abla, calcium carbonate, diatomaceous earth, silica, synthetic calcium silicate, kieselguhr, dolomite, powdered magnesia, Fuller's earth, gypsum and the like. Solid compositions can be in the form of dispersible powders or grains, comprising, in addition to COR, a surfactant to facilitate the dispersion of the powder or grains in liquid. Granular compositions can be prepared by, for example, impregnating COR onto or into granulated carriers such as attapulgites or vermiculites, or granulated solid fertilizers.

Liquid forms of the compositions of the invention, which are used for example, for spraying on fruit-bearing plants or trees as aerosols or mists, are prepared for application by admixing COR, surfactant, if used, and a liquid carrier, such as water or other liquid to form a stable emulsion or suspension. Liquid compositions of the invention include solutions, dispersions, or emulsions containing COR and optionally, one or more surface-active agents such as wetting agents, dispersing agents, emulsifying agents, or suspending agents.

Figure 2:
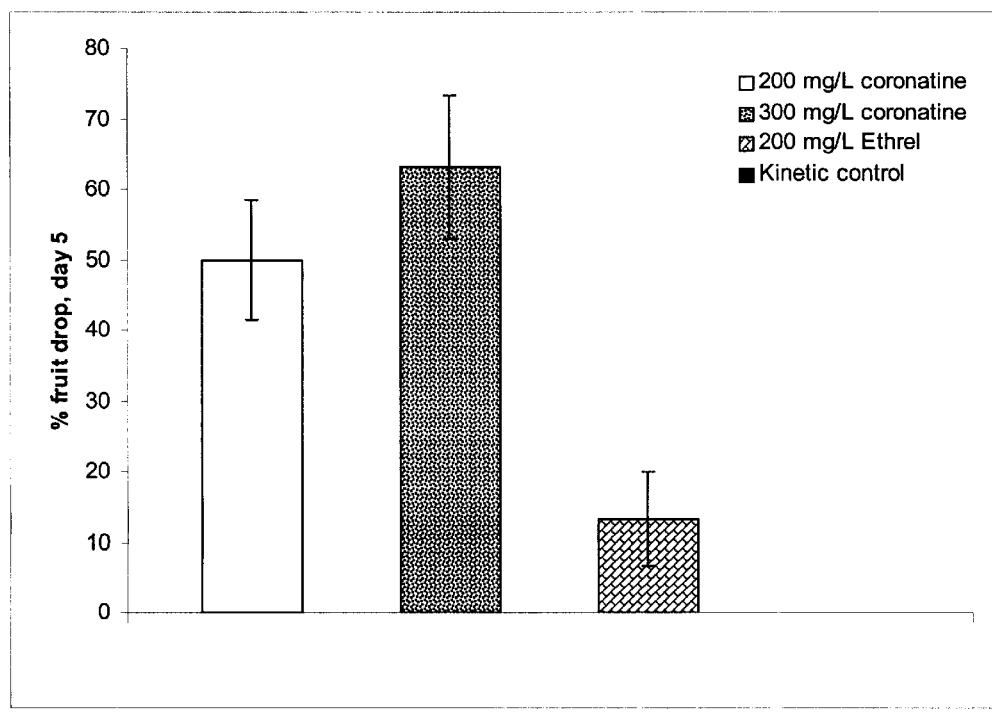
FIG. 2 demonstrates the effect of 200 mg/L and 300 mg/L coronatine, 200 mg/L Ethrel®, and a 0.125% Kinetic® alone treatment on percent fruit drop in Valencia orange. Data are the means of 10 replicate branches, with 10 fruit/branch. Bars above and below the means indicate standard error of the mean.
Figure 3:
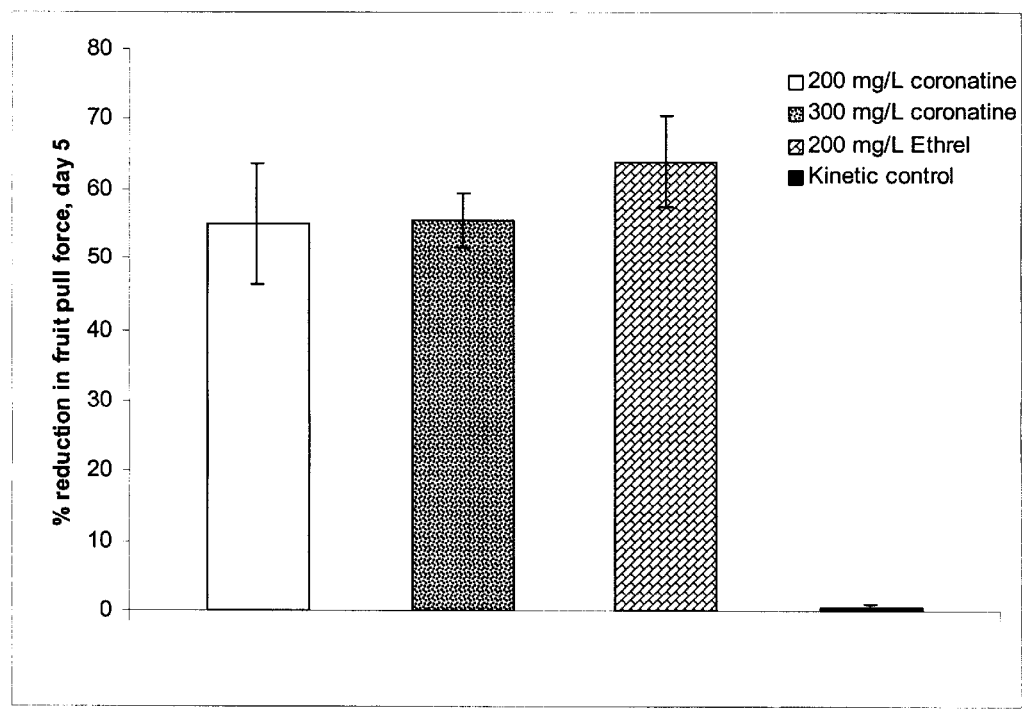
FIG. 3 demonstrates the effect of 200 mg/L and 300 mg/L coronatine, 200 mg/L Ethrel®, and a 0.125% Kinetic® alone treatment on percent reduction of fruit pull-force in Hamlin orange. Data are the means of 6 replicate branches, with 10 fruit/branch. Bars above and below the means indicate standard error of the mean.

COR compositions of the invention can be used alone or in a mixture with other abscission agents, thinning agents, plant hormones, or fertilizers. Abscission agents include, for example, Ethrel® (2-chloroethyl phosphonic acid) (Aventis), Ethephon® (Micro Flo Co., Memphis, Tenn.), Harvade® (Uniroyal Chemical Co., Middlebury, Conn.), FreeFall® (Griffin LLC, Valdosta, Ga.), and Folex® (Aventis). Thinning agents include, for example, naphthanlene acetic acid and Accel® (6-benzyladenine).

The compositions of the invention can also be used in plant-substantive formulations. Plant substantive formulations mechanically or chemically adhere to a plant and resist removal. Preferred plant substantive agents include various waxes and paraffins, polymers, and sulfur. Wax coated compositions can be prepared by dispersing COR in molten wax, forming the dispersion into small particles, and cooling the composition below the melting point of the wax. The water resistance of the particles can be controlled by increasing or decreasing the amount of wax employed so as to provide proper release for climatic conditions, i.e., wet areas or dry areas. Additionally, various additives can be dissolved in the wax phase in order to improve the water resistance of the composition or effect other benefits such as slow-release additives or anticaking agents. Other plant-substantive agents include casein, salts of alginic acids, cellulose gums and their derivatives, polyvinyl pyrrolidone, vegetable gums, porpylene glycol, invert syrup, corn syrup, and the like.

Administration of COR

When fruit has reached substantial maturity, a composition of the invention is applied, generally 3 to 20 days prior to harvest, and preferably 3 to 10 days prior to the harvesting date, by administration to the fruit locus or to the whole plant or tree. Optionally, two or more applications of compositions can be done at different times prior to harvest. Preferably, application is by high volume spray, to run-off.

Preferably, the concentration of COR in a composition of the invention is about 10 mg/L to about 1,000 mg/L. More preferably, the concentration of COR is about 50 mg/L to about 500 mg/L. Even more preferably, the concentration of COR is about 100 mg/L to about 300 mg/L. Typically, a 5.0 L solution of COR at these concentrations can treat, for example, a 15 foot citrus tree. Although grove density and tree size varies, an acre of citrus grove contains approximately 120 trees. Therefore, about 600 L are used to treat an acre of citrus trees.

Harvesting is accomplished by exerting sufficient force on the fruit to separate the fruit from the tree or plant. Harvesting can be accomplished using manual (e.g., hand harvesting) or mechanical methods.

Fruit-bearing plants or trees of the invention include the major types of fruit for example, berries such as grapes, blueberries, and oranges; drupes such as peaches, cherries, olives, plums and walnuts; aggregate fruit such as blackberries and raspberries; multiple fruit such as pineapples, figs and mulberries; and accessory fruit such as apples, pears and strawberries. Also included are cotton plants. Preferred fruit of the invention are citrus fruit such as oranges, grapefruit, kumquats, lemons, limes, tangerines, temples, citrange, tangelo, pomelo, and citron.

The following are provided for exemplification purposes only and are not intended to limit the scope of the invention described in broad terms above. All references cited in this disclosure are incorporated herein by reference.

EXAMPLES

Example 1

Solutions of COR were prepared that contained 200 mg/L or 300 mg/L of COR dissolved in water and 0.125% Kinetic®. The solution was sprayed until "run-off," typically about 5 L/tree. The solution wetted the foliage and fruit, but did not excessively run-off to the ground. Under field conditions, canopies should not be sprayed if rainfall is anticipated within 24 hours. For comparison purposes, 200 mg/L to 400 mg/L Ethrel® solutions and a 0.125% Kinetic® solution were applied to trees. After several days, usually 3 to 10, differences in fruit pull-force were measured between COR and other treatments and is an indication of fruit loosening ability. See FIGS. 1 and 3 and Tables 1 and 3, which demonstrate in Valencia and Hamlin orange varieties, respectively, that COR compositions were effective in reducing fruit pull-force by approximately 95% and were substantially more effective than Ethrel® and the control. Differences in fruit drop were also measured by counting or weighing dropped fruit. See FIG. 2 and Table 2, which demonstrate in Valencia orange that COR compositions substantially increased the percentage of fruit drop as compared to Ethrel® and the control.

TABLE 1

Effect of COR on percent reduction of fruit pull force in Valencia Orange.

| Treatment | % reduction in fruit pull force, day 5 | SE mean |
|---|---|---|
| 200 mg/L COR | 96.1 | 0.3 |
| 300 mg/L COR | 96.3 | 0.3 |
| 200 mg/L Ethrel ® | 71.7 | 3 |
| Kinetic ® control | 6.1 | 2.5 |

TABLE 2

Percent fruit drop in Valencia orange treated with COR.

| Treatment | % fruit drop, day 5 | SE mean |
|---|---|---|
| 200 mg/L COR | 50 | 8.5 |
| 300 mg/L COR | 63.3 | 10.1 |
| 200 mg/L Ethrel ® | 13.3 | 6.6 |
| Kinetic ® control | 0 | 0 |

TABLE 3

Effect of COR on percent reduction of fruit pull force in Hamlin orange.

| Treatment | % reduction in fruit pull force, day 5 | SE mean |
|---|---|---|
| 200 mg/L COR | 55 | 8.6 |
| 300 mg/L COR | 55.5 | 3.9 |
| 200 mg/L Ethrel ® | 64 | 6.6 |
| Kinetic ® control | 0.6 | 0.4 |

We claim:

1. A composition for inducing abscission comprising coronatine and one or more surfactants.

2. The composition of claim 1, wherein the surfactant is sorbitan mono-9 octadecenoate poly(oxy-1,1-ethanedlyl).

3. The composition of claim 2, wherein volume by volume of the surfactant is about 1.0% to about 0.01%.

4. The composition of claim 1, wherein the surfactant is a blend of poloyalkylene oxide modified polydimethyl siloxane and non-ionic surfactant.

5. The composition of claim 4, wherein volume by volume of the surfactant is about 1.0% to about 0.01%.

6. The composition of claim 1, wherein the concentration of coronatine is about 10 mg/L to about 1,000 mg/L.

7. The composition of claim 1, wherein the concentration of coronatine is about 50 mg/L to about 500 mg/L.

8. The composition of claim 1, wherein the concentration of coronatine is about 100 to about 300 mg/L.

9. A method of inducing fruit abscission comprising administering an effective amount of coronatine to a fruit-bearing plant or tree, whereby fruit abscission is induced.

10. The method of claim 9, wherein the fruit is citrus.

11. The method of claim 10, wherein the citrus is orange.

12. The method of claim 9, wherein the fruit is apple.

13. The method of claim 9, wherein the fruit is cherry.

14. The method of claim 9, wherein the concentration of coronatine is about 10 mg/L to about 1,000 mg/L.

15. The method of claim 9, wherein the concentration of coronatine is about 50 mg/L to about 500 mg/L.

16. The method of claim 9, wherein the concentration of coronatine is about 100 mg/L to about 300 mg/L.

17. A method of harvesting fruit from a plant or tree comprising:

(a) administering an effective amount of coronatine to a fruit-bearing plant or tree; and (b) exerting sufficient force on the fruit to separate the fruit from the plant or tree.

18. The method of claim 17, wherein the fruit is citrus.

19. The method of claim 18, wherein the citrus is orange.

20. The method of claim 17, wherein the fruit is apple.

21. The method of claim 17, wherein the fruit is cherry.

22. The method of claim 17, wherein the concentration of coronatine is about 10 mg/L to about 1,000 mg/L.

23. The method of claim 17, wherein the concentration of coronatine is about 50 mg/L to about 500 mg/L.

24. The method of claim 17, wherein the concentration of coronatine is about 100 to about 300 mg/L.

25. The method of claim 17, wherein the method of harvesting is selected from the group consisting of manual harvesting and mechanical harvesting.

\* \* \* \* \*